US012496410B2

(12) United States Patent
Dombrowski et al.

(10) Patent No.: US 12,496,410 B2
(45) Date of Patent: Dec. 16, 2025

(54) TAMPER-EVIDENT CLOSURE

(71) Applicant: Solventum Intellectual Properties Company, Maplewood, MN (US)

(72) Inventors: Alan R. Dombrowski, Woodbury, MN (US); Adam S. Troness, Dellwood, MN (US); Jack E. Kochevar, Minneapolis, MN (US); Dennard J. Powell, Saint Paul, MN (US); Michael J. Vostal, Minneapolis, MN (US); Matthew T. Zabel, Lake Elmo, MN (US); Jacqueline M. Ganser, White Bear Lake, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 975 days.

(21) Appl. No.: 17/629,433

(22) PCT Filed: Jul. 31, 2020

(86) PCT No.: PCT/IB2020/057293

§ 371 (c)(1),
(2) Date: Jan. 24, 2022

(87) PCT Pub. No.: WO2021/024139

PCT Pub. Date: Feb. 11, 2021

(65) Prior Publication Data

US 2022/0241520 A1 Aug. 4, 2022

Related U.S. Application Data

(60) Provisional application No. 62/981,202, filed on Feb. 25, 2020, provisional application No. 62/934,884, (Continued)

(51) Int. Cl.
*A61M 5/50* (2006.01)
*A61M 5/00* (2006.01)
(Continued)

(52) U.S. Cl.
CPC .......... *A61M 5/5086* (2013.01); *A61M 5/002* (2013.01); *A61M 39/162* (2013.01); *A61M 39/20* (2013.01); *A61M 39/0247* (2013.01)

(58) Field of Classification Search
CPC ...... A61M 5/5086; A61M 5/002; A61M 5/14; A61M 25/02; A61M 39/165;
(Continued)

(56) References Cited

U.S. PATENT DOCUMENTS 4,286,640 A 9/1981 Knox
5,531,695 A 7/1996 Swisher
5,830,195 A * 11/1998 Peters ................ A61M 39/286
604/905
7,282,186 B2 10/2007 Lake, Jr.
(Continued)

FOREIGN PATENT DOCUMENTS

CN 206645269 U 11/2017
EP 0 344 942 A2 12/1989
(Continued)

OTHER PUBLICATIONS

International Search Report for PCT International Application No. PCT/IB2020/057293, mailed on Jan. 15, 2021, 7 pages.

*Primary Examiner* — Lauren P Farrar
*Assistant Examiner* — Alexandra E Lalonde

(57) ABSTRACT

A tamper-evident closure is disclosed that encloses a medical access device, such as a vascular access device, such that it will be visibly apparent if the medical access device contained in the tamper-evident closure becomes exposed. The tamper-evident closure cannot be reapplied over the medical access device in a way to look the same as it did prior to exposing the medical access device. The tamper-evident closure comprises a holding cavity, a securing mechanism, and an apparent release. The disclosed tamper-evident closure is well suited for securing the medical access device that has an access point for delivering fluid to a patient or removing fluid from the patient.

18 Claims, 17 Drawing Sheets

Related U.S. Application Data filed on Nov. 13, 2019, provisional application No. 62/924,201, filed on Oct. 22, 2019, provisional application No. 62/882,133, filed on Aug. 2, 2019.

(51) Int. Cl.

| | |
|---|---|
| ***A61M 39/16*** | (2006.01) |
| ***A61M 39/20*** | (2006.01) |
| *A61M 39/02* | (2006.01) |

(58) Field of Classification Search

CPC ........................ A61M 39/1011; A61M 39/162; A61M 39/20; A61M 39/0247; A61M 2205/583; A61M 2025/0206; A61M 2025/026; A61M 2025/0266; A61M 5/50; A61M 5/158; A61M 2025/028; A61M 2025/0246; A61M 2025/0253; A61M 2025/0273; A61M 2005/1586; Y10S 604/905; Y10S 128/26

See application file for complete search history.

(56) References Cited

U.S. PATENT DOCUMENTS

| | | | | |
|---|---|---|---|---|
| 7,780,794 | B2 | 8/2010 | Rogers | |
| 9,259,284 | B2 | 2/2016 | Rogers | |
| 9,907,617 | B2 | 3/2018 | Rogers | |
| 10,722,662 | B1 * | 7/2020 | Mench | G09F 3/0311 |
| 2010/0252618 | A1 | 10/2010 | Adam et al. | |
| 2014/0303595 | A1 | 10/2014 | Justus et al. | |
| 2015/0006045 | A1 | 1/2015 | Chou | |
| 2017/0016543 | A1 | 1/2017 | Lopansri et al. | |
| 2017/0065808 | A1 * | 3/2017 | Filz | A61M 39/18 |
| 2017/0157384 | A1 * | 6/2017 | Christie | A61M 39/1011 |
| 2017/0283139 | A1 | 10/2017 | Fosse | |

FOREIGN PATENT DOCUMENTS

| | | | |
|---|---|---|---|
| WO | 1995022369 | A1 | 8/1995 |
| WO | WO 1995-022369 | | 8/1995 |
| WO | 2016/046838 | A2 | 3/2016 |

* cited by examiner

TAMPER-EVIDENT CLOSURE

CROSS REFERENCE TO RELATED APPLICATIONS

This application is a national stage filing under 35 U.S.C. 371 of PCT/IB2020/057293, filed Jul. 31, 2020, which claims the benefit of U.S. Provisional Application No. 62/882,133, filed Aug. 2, 2019; U.S. Provisional Application No. 62/924,201, filed Oct. 22, 2019; U.S. Provisional Application No. 62/934,884, filed Nov. 13, 2019; and U.S. Provisional Application No. 62/981,202, filed Feb. 25, 2020; the disclosures of which are incorporated by reference in their entirety herein.

TECHNICAL FIELD

The present disclosure relates to a tamper-evident closure. In particular, the present disclosure relates to a tamper-evident closure for medical access devices, such as intravenous access points.

BACKGROUND

Patients receiving medical care will commonly have a medical access device, such as a vascular access device, inserted to assist the healthcare provider in delivering medications to the patient. Some medical access devices are for allowing fluids to be removed from a patient, like a urinary catheter or a surgical drain line. When a person is under the care of a healthcare provider it is important to control the medications that are delivered to the patient. Patients with psychiatric conditions, intellectually delayed patients, pediatric patients, or intravenous drug users may tamper with intravenous access points or intentionally deliver drugs or medications to the vascular access device. Unprescribed drugs entering the vascular access device can cause medical problems, drug interactions, blood stream infections.

SUMMARY

The disclosed tamper-evident closure encloses a medical access device. It will be visibly apparent that the tamper-evident closure has been modified if the medical access device contained in the tamper-evident closure becomes accessed. The tamper-evident closure cannot be reapplied over the medical access device in a way to look the same as it did prior to exposing the medical access device.

In some embodiments, depending on the selection of materials used, the tamper-evident closure also serves as a tamper-proof closure. With a tamper-proof closure, without the release mechanism, the medical access device is not accessible and cannot be exposed.

Disclosed are various tamper-evident closures. The tamper-evident closures comprise a holding cavity, a securing mechanism, and an apparent release. The disclosed tamper-evident closures are well suited for securing a medical access device that has an access point for delivering fluid to a patient or removing fluid from a patient.

Figure 1A:
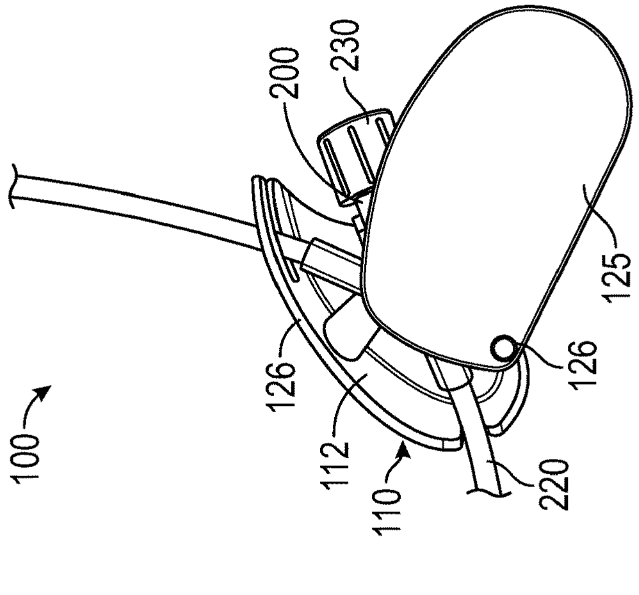
FIG. 1*a* is a perspective view of one embodiment of a front side of a tamper-evident closure showing the exterior cover open to expose the contained vascular access device.

While the above-identified drawings and figures set forth embodiments of the invention, other embodiments are also contemplated, as noted in the discussion. In all cases, this disclosure presents the invention by way of representation and not limitation. Numerous other modifications and embodiments can be devised by those skilled in the art, which fall within the scope and spirit of this invention. The figures may not be drawn to scale.

DETAILED DESCRIPTION

Various designs for tamper-evident closures are disclosed. The disclosed tamper-evident closure 100 comprises a holding cavity 110, a securing mechanism 160 such that upon tampering or removal of the securing mechanism there is a visually apparent indication that the holding cavity 110 has been opened or the securing mechanism 160 has been released. The disclosed tamper-evident closures are well suited for securing a medical access device 200 that has an access point 210 for delivering fluid to a patient, removing fluid from a patient or connecting to other devices through a tube 220. In some embodiment, caps 230, such as a 3M™ Curos™ Disinfecting Cap that contain disinfectant are secured over the access point 210.

The holding cavity 110 typically has a perimeter 111 surrounding at least a portion of a central area 112 with an access point 113 into the central area 112. Typically, the tamper evident closure 100 can be open to all the access device 200 to be placed in the holding cavity 110 and closed to secure the access device 200 within the holding cavity 110. A securing mechanism 160 160 retains the tamper evident closure 100 closed. Various design of the holding cavity 110 and securing mechanism 160 are contemplated and disclosed herein.

The holding cavity 110 of the tamper-evident closure 100 contains the medical access device 200. The medical access device 200 can be any site on a catheter or intravenous tubing where medications can be administered and/or where fluid can be removed. The medical access device 200 can be a vascular access device that is a connection to the patient's vascular system for either administering medication or removing blood. The medical access device 200 can be any portion of the infusion tubing, catheter, tube, or other medical device. This can be any site on a catheter, intravenous tubing, or other topical or percutaneous medical device. This may be a luer active device ("LAD") on a y-site, a LAD on the end of a line, or a male/female connection in the middle of the line or any other connection used on a topical or percutaneous medical device. A luer activated device can be either capped or un-capped.

When the holding cavity 110 is closed by the securing mechanism 160, the fluid access point 210 for the medical access device 200 is inaccessible. Only when the apparent release is actuated will the fluid access point (covered by cap 230) of the medical access device 200 become accessible, but when the apparent release is actuated it will be visibly apparent that the tamper-evident closure 100 has been opened.

In some embodiments like shown in the figures, the fluid access point contains a cap 230 for covering the fluid access point prior to use. Caps 230 can contain a disinfecting agent to keep the fluid access point 210 clean until use. Exemplary caps 230 are described in U.S. Pat. Nos. 7,282,186; 7,780,794; 9,907,617; 9,259,284, the disclosures of which are herein incorporated by reference. Exemplary caps 230 are sold as 3M™ CUROS™ Disinfecting Caps for Needleless Connectors, available from 3M Company.

In some embodiment, materials that are highly resistant to breaking by cutting or impact, such as plastics, films, metals or ceramics, could be used to make the tamper-evident closure a tamper-resistant or even tamper-proof closure.

In the embodiments shown in FIGS. 1-15, the medical access device 200 is a vascular access device. It is understood that other medical access devices may be used in the tamper-evident closure 100.

Figure 1B:
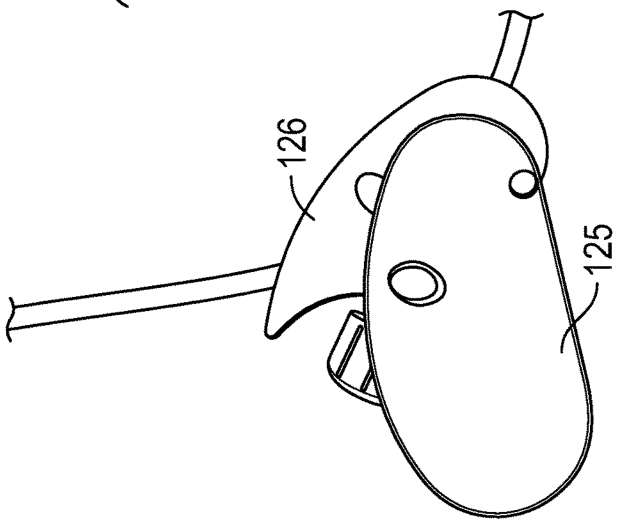
FIG. 1*b* is a perspective view of the rear side of the tamper-evident closure of FIG. 1*a;*
Figure 1C:
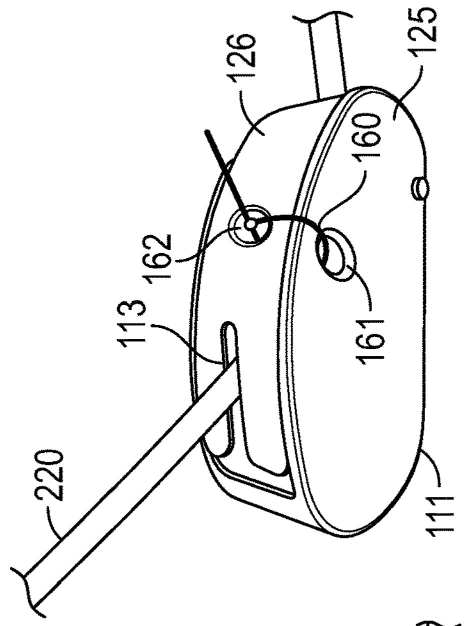
FIG. 1*c* is a perspective view of the tamper-evident closure of FIG. 1*a* showing the exterior cover closed to contain the vascular access device.

FIG. 1*a* is a perspective view of one embodiment of a front side of a tamper-evident closure 100 in an open position to expose the contained vascular access device 200. FIG. 1*b* is a perspective view of the rear side of the tamper-evident closure 100 of FIG. 1*a*. FIG. 1*c* is a perspective view of the tamper-evident closure 100 of FIG. 1*a* in a closed position to contain the vascular access device 200.

In this embodiment, the holding cavity 110 of the tamper-evident closure 100 is a box 120 and comprises a first part 125 and a second part 126 connected together at a pivot so that the first part 125 can be moved relative to the second part 126 to open the tamper-evident closure 100 to expose the holding cavity 110. There are access points 113 in the tamper-evident closure 100 to allow the vascular access device tubing 220 to exit from the holding cavity 110 while the vascular access device 200 is contained within the holding cavity 110. The access points 113 can be slightly narrower than standard flexible tubing 220 to hold the tubing 220 in place so the vascular access device 200 stays securely positioned while the first part 125 pivots relative to the second part 126. In this embodiment, the access points 113 are both on the first part 125 and second part 126 so when secured together the user can access the tubing 220 with one hand while keeping the vascular access device secure.

As can be seen in FIG. 1*b*, there is a through-hole 161 in the first part 125 and a through-hole 162 in the second part 126, such that the through-holes can align to create a continuous channel A securing mechanism 160, such as a one-way tie down passes through the continuous channel to prevent the first part 125 from moving relative to the second part 126 to maintain the holding cavity 110 closed. The holding cavity 110 will become exposed when either the entire tamper-evident closure 100 is destroyed or when the securing mechanism 160 is broken. Either way, tampering would be evident. To break the securing mechanism 160, hand pressure could break the line, the device may include a cutting tool or the health care provider can use a cutting tool, such as scissors.

This embodiment, rigid materials for the first and second parts 125, 126 and securing mechanism 160 could be used to make this a tamper-resistant or tamper-proof holding cavity for the vascular access device.

Figure 2A:
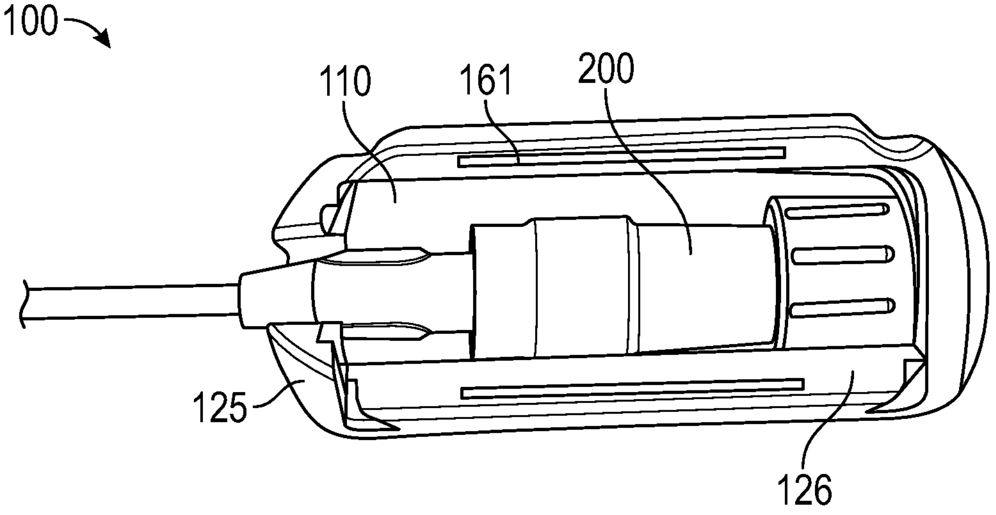
FIG. 2*a* is a perspective view of another embodiment of a tamper-evident closure for a vascular access device showing a sliding cover retracted exposing the contained vascular access device.
Figure 2B:
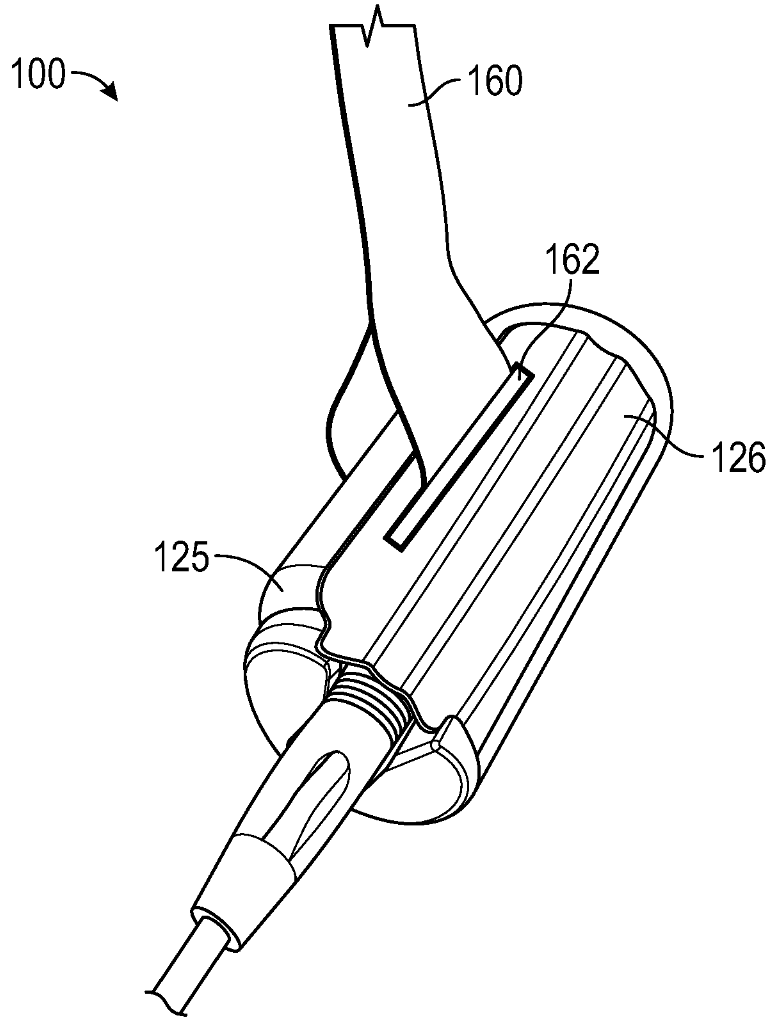
FIG. 2*b* is a perspective view of the tamper-evident closure of FIG. 2*a* showing the sliding cover closed to contain the vascular access device.

FIG. 2*a* is a perspective view of another embodiment of a tamper-evident closure 100 for a vascular access device 200 showing a sliding cover retracted exposing the contained vascular access device 200. FIG. 2*b* is a perspective view of the tamper-evident closure 100 of FIG. 2*a* showing the sliding cover 121 closed and a securing mechanism 160 to maintain the sliding cover closed.

This embodiment is similar to the embodiment in FIGS. 1*a*-1*c* except that the first part 125 and second part 126 that form the holding cavity 110 are slidably connected. The second part 126 functions like a door and slides from an open position (FIG. 2*a*) to a closed position (FIG. 2*b*) while wrapping around the cylindrical body of the first part 125. This allows a minimal size holding cavity 110 with a sliding door 121 since the door "wraps" around the first part. The first part 125 is rounded to eliminate any sharp edges to improve patient comfort. First through-hole 161 in the first part 125 and second through-hole 162 the second part 126 align to create a continuous channel. In this embodiment, the continuous channel is a thin, longitudinally extending passage. The securing mechanism 160 shown in 2*b*, is an adhesive tape passing, passes through the continuous channel to prevent the second part from opening. The holding cavity 110 will become exposed when either the entire tamper-evident closure is destroyed or when the securing mechanism 160 is broken.

As shown, the holding cavity 110 of the tamper-evident enclosure 100 can be of various sizes, and include access points 113 at various location, to accommodate various configurations of vascular access devices 200. The continuous channel can be of various sizes and shapes to accommodate a securing mechanism 160 that will connect from one side of the continuous channel on the first part to the other side of the continuous channel on the second part.

Figure 3A:
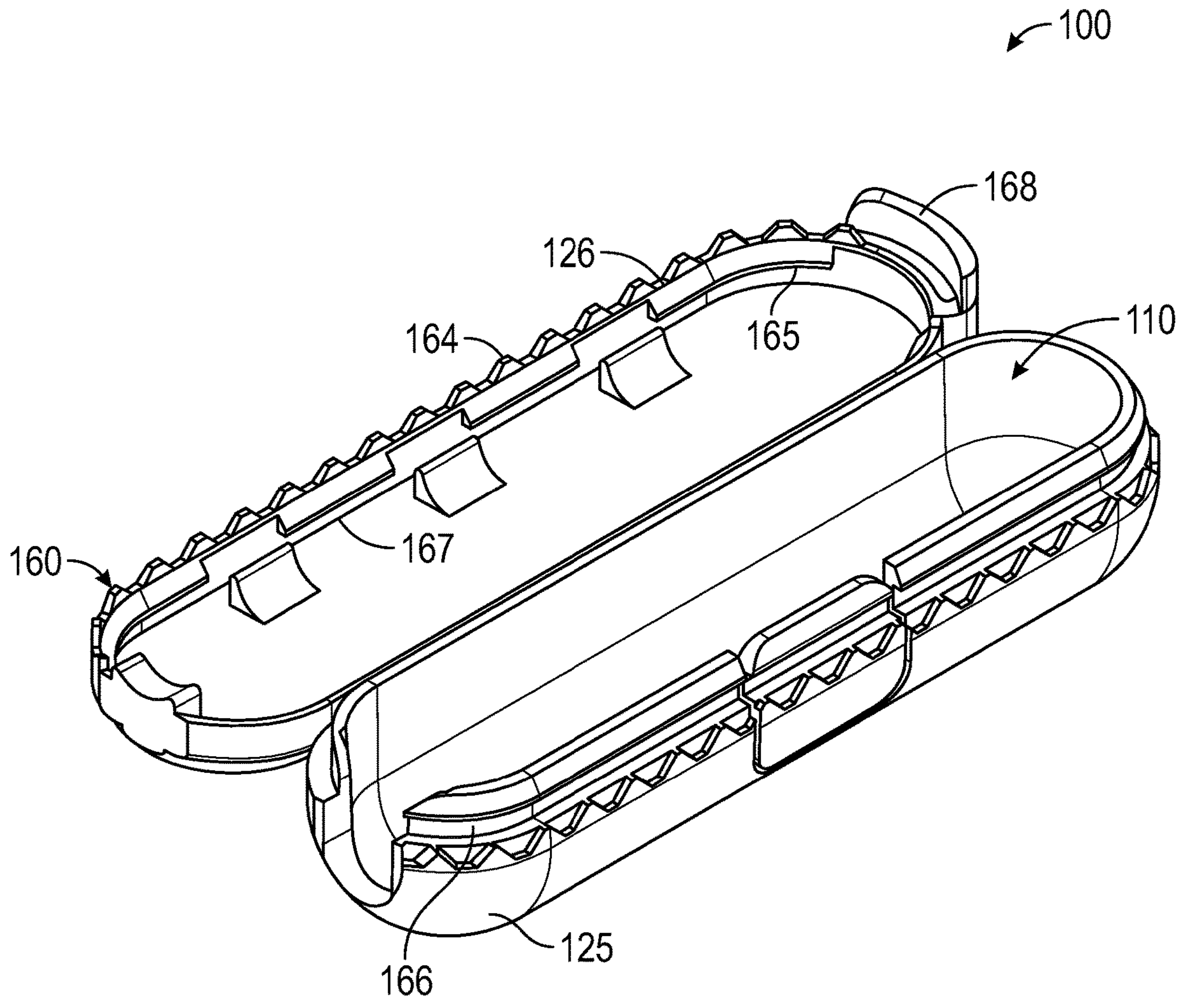
FIG. 3*a* is a perspective view of another embodiment of a tamper-evident closure comprising a two-part locking device in an open position.
Figure 3B:
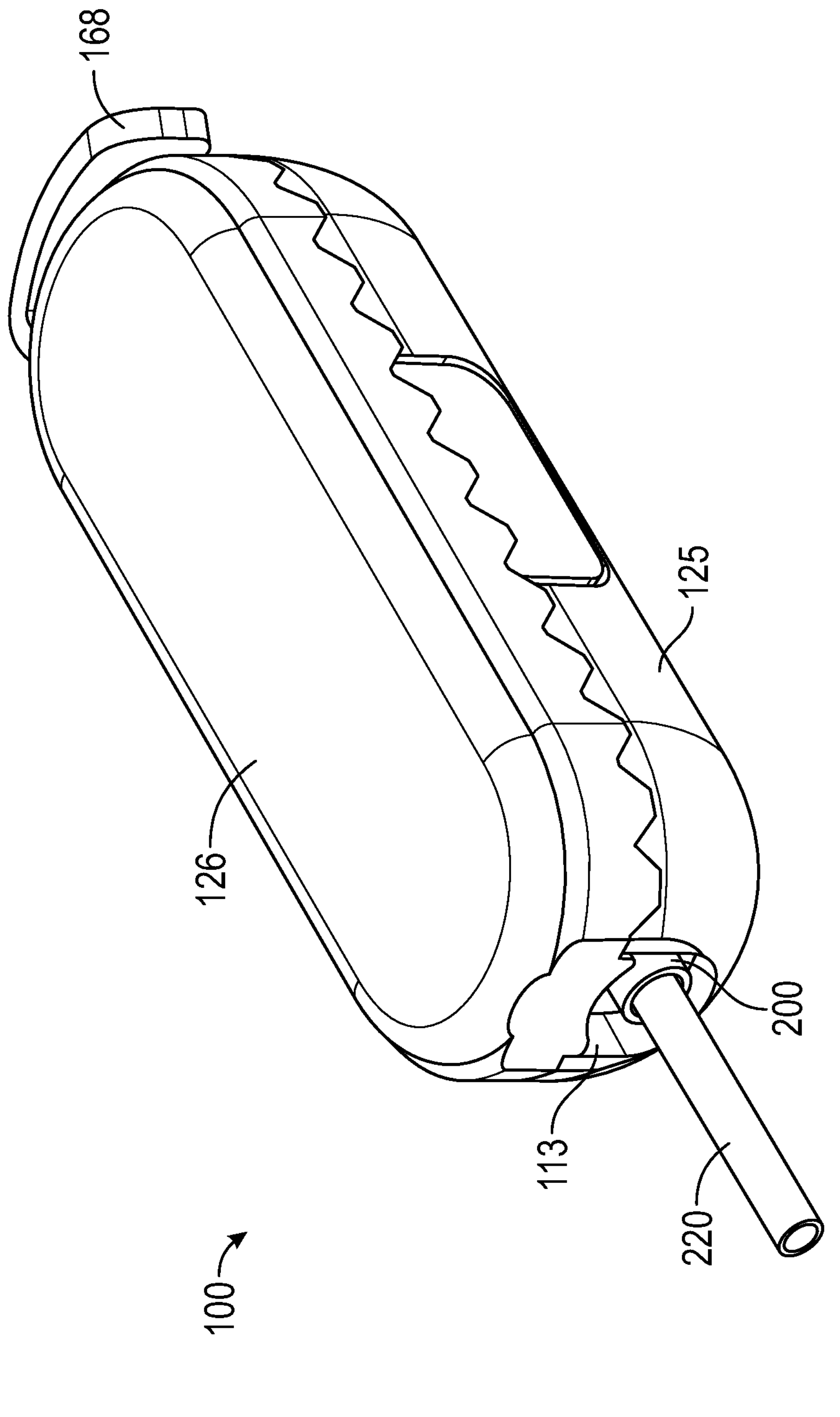
FIG. 3*b* is a perspective view of the tamper-evident closure of FIG. 3*a* with the two-part locking device locked in a closed position and containing the vascular access device.

FIG. 3*a* is a perspective view of another embodiment of a tamper-evident closure comprising a holding cavity with a first part and a second part. FIG. 3*b* is a perspective view of the tamper-evident closure of FIG. 3*a* in a closed position, locked and containing the vascular access device.

In this embodiment, the tamper-evident closure 100 comprises a first part 125 and a second part 126 that connect together to form the holding cavity 110. The vascular access device 200 is placed in the first part 125, and then the second part 126 overlies the first part 125 and pressed to lock with the first part 125, like shown in FIG. 3*b*. The first part 125 and second part 126 can be two separate parts or could be connected to one another by a hinge. There are access points 113 in the tamper-evident closure 100 to allow the vascular access devices tubing 220 to exit from the holding cavity 110 while the vascular access device 200 is contained within the holding cavity 110.

The securing mechanism 160 comprises a channel locking fit 164 extends around at least a portion of the perimeter of the tamper-evident closure 100 connecting the first part 125 and second part 126. The channel locking fit 164 has a line of weakness 167 adjacent to the channel locking fit 164, and a tab 168. The channel locking fit 164 comprises a longitudinally extending protruding portion 165 on one of the first or second parts 125, 126, and a longitudinally extending receiving portion 166, interlocking with the protruding portion 165, on the other of the first or second parts 125, 126. In this embodiment, the channel locking fit 164 is a zig-zag line, which can give additional strength to the device and limit a user from prying open the device with a tool. For example, the short lengths do not easily allow for an edge of a tool like a screwdriver or knife to press between and separate. Also along the securing mechanism 160, on a side of the securing mechanism 160 opposite the channel locking fit 164, is the line of weakness 167, which could be thin or perforated portion connecting the securing mechanism 160 to the first part or second part 125, 126. Extending from the securing mechanism 160 is a tab 168 for separating the channel locking fit 164.

For example, the securing mechanism 160 in this embodiment is connected to the second part 126 by the line of weakness 167. On the side of the securing mechanism 160 opposite the line of weakness 167 is the longitudinally extending protruding portion 165. On first part 125 is the longitudinally extending receiving portion 166. The channel locking fit 164 interlocks the first part 125 to the second part 126, as shown in FIG. 3*b*.

To remove the securing mechanism 160, the tab 168 is pulled to break the line of weakness 167. This alone would be sufficient to disengage the locking connection between the first part 125 from the second part 126. The holding cavity 110 will become exposed when either the entire tamper-evident closure 110 is destroyed, or when the tab 168 is at least partially removed from the tamper-evident closure 100 and the line of weakness 167 is broken. Either way, tampering would be evident.

Figure 3C:
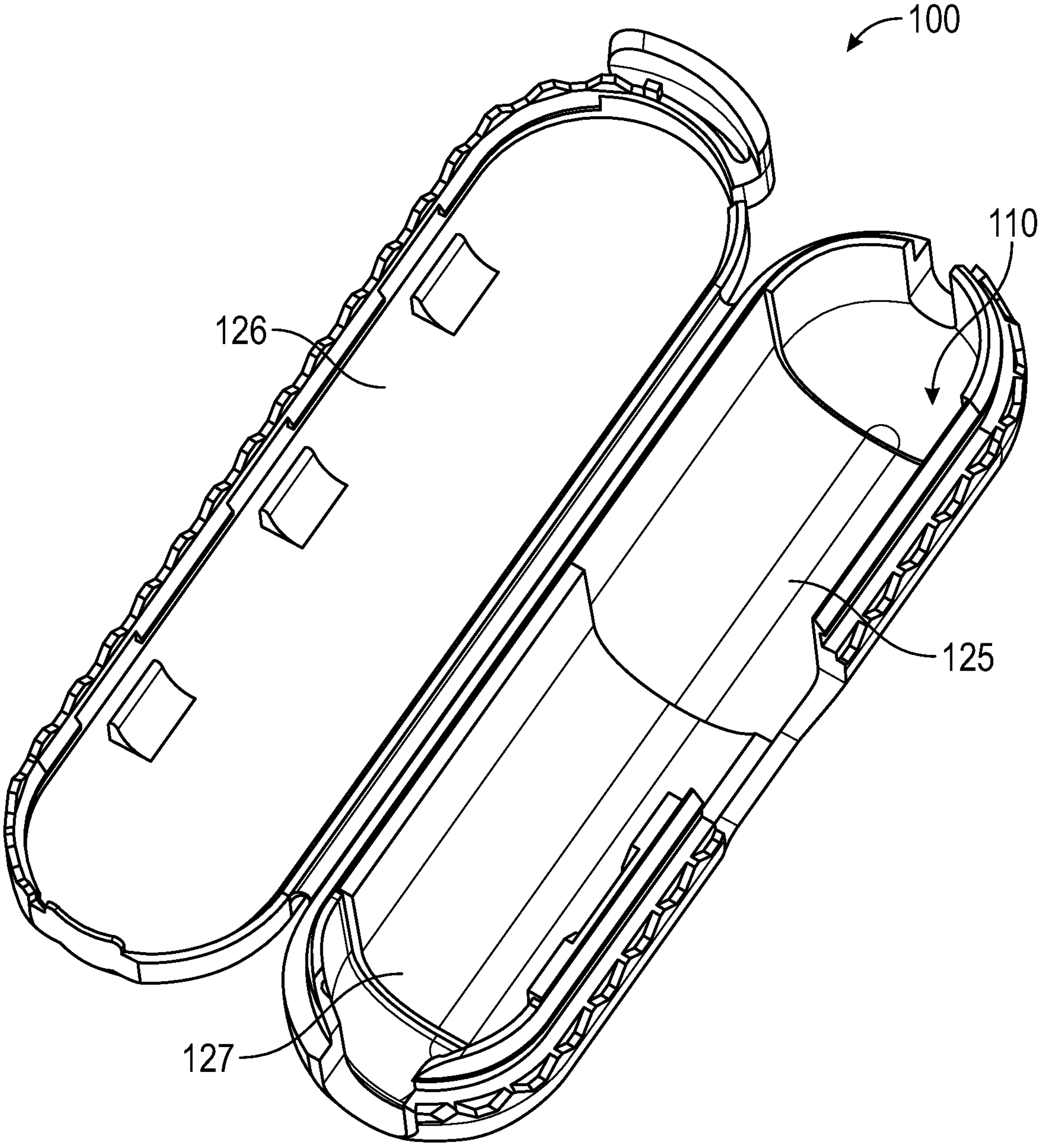
FIG. 3*c* is a perspective view of another embodiment of a tamper-evident closure with a sliding door covering an access point.
Figure 3D:
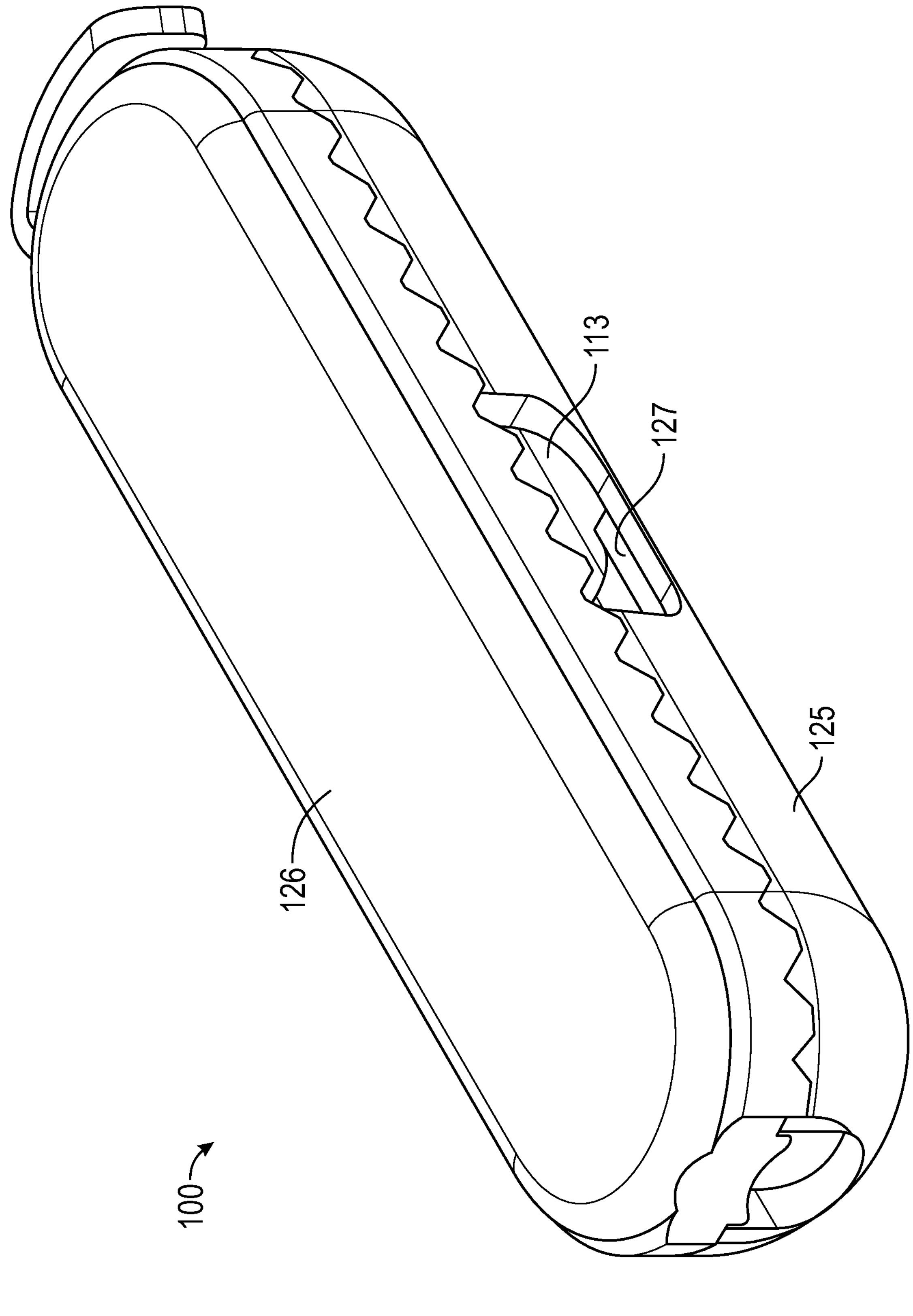
FIG. 3*d* is a perspective view of the tamper-evident closure of FIG. 3*c* in a closed position with the sliding door open providing an opening to an access point.

FIG. 3*c* is a perspective view of another embodiment of a tamper-evident closure 100 in an open position showing an internal sliding door 127, and FIG. 3*d* is the tamper-evident closure 100 from FIG. 3*c* in a closed position with. The tamper-evident closure 100 is substantially similar to the tamper-evident closure from FIGS. 3*a*, 3*b*. In both FIG. 3*c* and FIG. 3*d*, the internal sliding door 127 is open to expose an access point 113 to the holding cavity. The sliding door 127 is within the first part 125 and can be slidably actuated to open or close the access point 113 if the vascular access device has a "Y" line.

Figure 4:
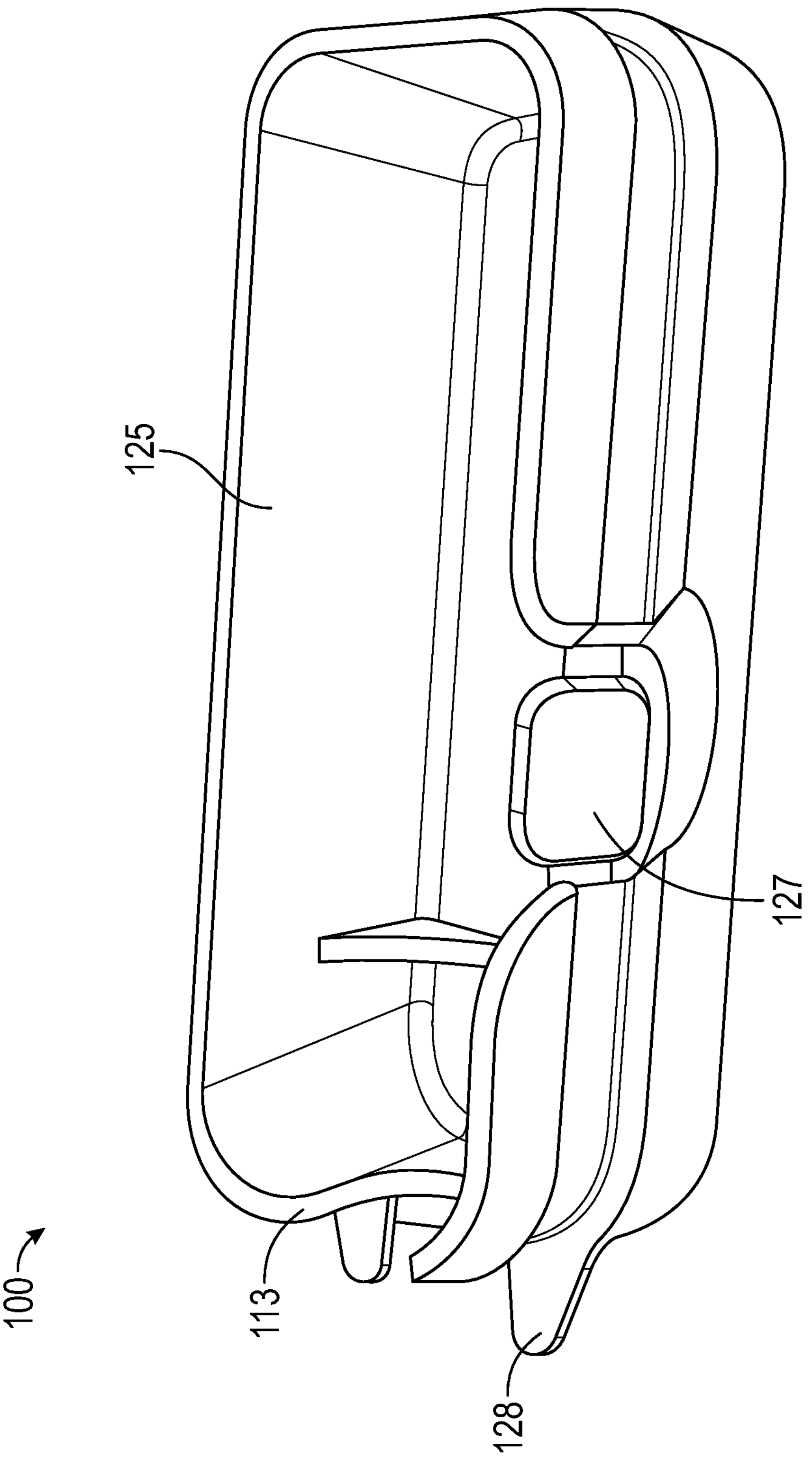
FIG. 4 is a perspective view of another embodiment of a tamper-evident closure comprising removable door.

FIG. 4 is a perspective view of another embodiment of a tamper-evident closure 100 comprising removable door 127. This removable door 127 includes thin portions connecting the removable door 127 to the first part 125 so that it could be easily removed to open the access point 113 if the vascular access device has a "Y" line.

In the embodiments shown in FIG. 4, front tabs 128 are included. These front tabs 128 are spaced apart from one another on each side of the access point 113. In this embodiment, the front tabs 128 are located on the exterior of the tamper evident closure 100 to fit against the wings of a protruding vascular access device to prevent the vascular access device from rotating. It could be possible that rotating could allow for tampering of the contain vascular access device, by unthreading or disconnecting the device.

The sliding door, removable door, or front tabs can be used on any number of the disclosed tamper-evident enclosures.

Figure 5B:
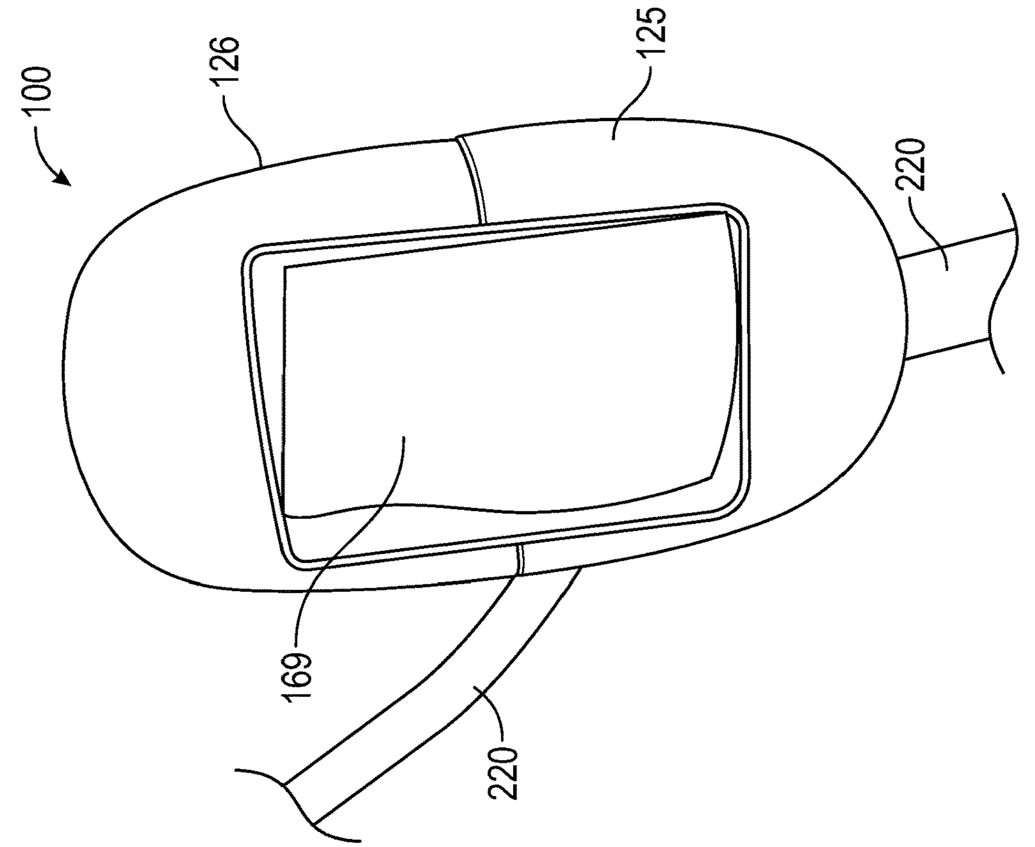
FIG. 5*b* is a perspective view of the tamper-evident closure of FIG. 5*a* rotated to a closed position and with a security sticker applied to the aligned region of the two part rotatably connected device.
Figure 5A:
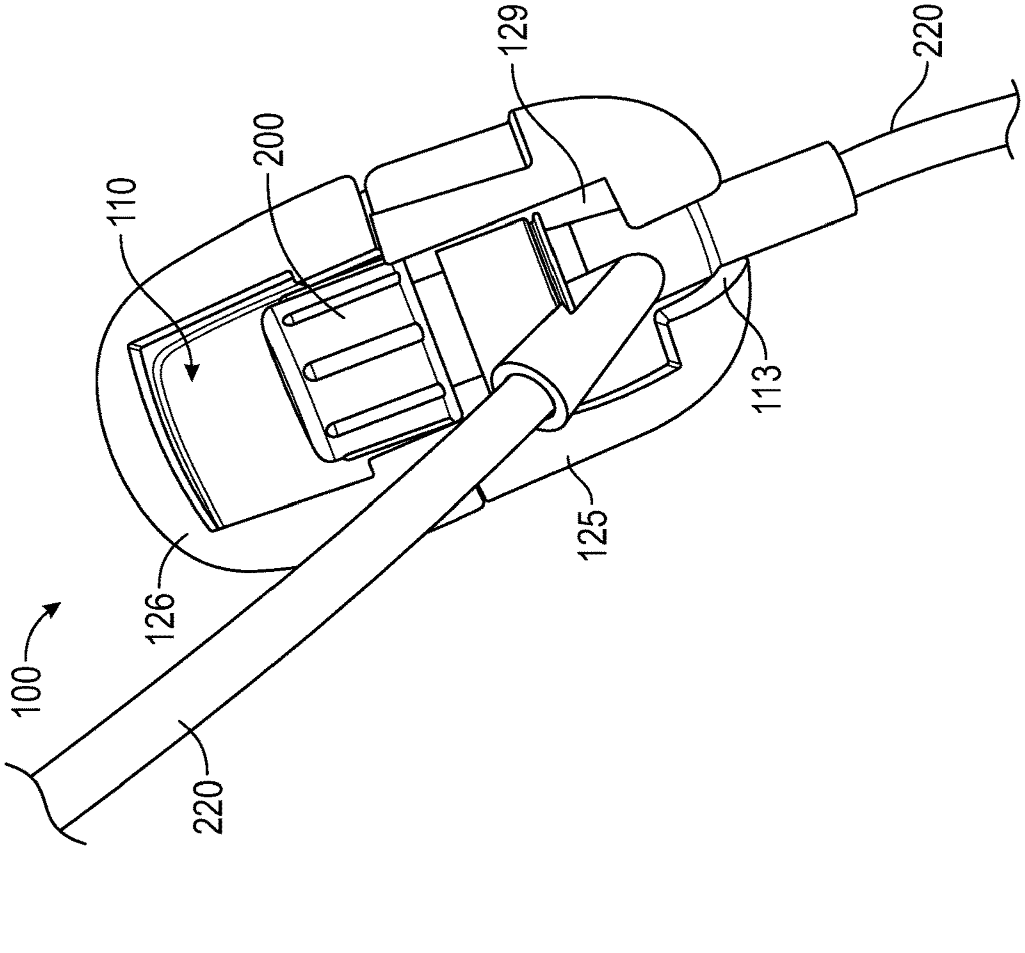
FIG. 5*a* is a perspective view of another embodiment of a tamper-evident closure comprising a two part rotatably connected device with a vascular access device in a first part.

FIG. 5*a* is a perspective view of another embodiment of a tamper-evident closure 100 comprising box 120 having a first part 125 and second part 126 rotatably connected to form the holding cavity 110. FIG. 5*b* is a perspective view of the tamper-evident closure 100 of FIG. 5*a* with the first part 125 and second part 126 rotated to close the holding cavity 110 and with the securing mechanism 160, which comprises a security sticker 169 to hold the tamper-evident closure 100 closed.

In this embodiment, the holding cavity 110 is formed from a first part 125 and second part 126 that are rotatably connected together. As shown, extending from an end is an access point 113 for the tubing 220. An open portion 129 is formed when the first part 125 and second part 126 are rotated as shown in FIG. 5*a* so the vascular access device 200 can be inserted in to the holding cavity 110. Then, the first part 125 and second part 126 are rotated to disconnect the mis-align the open portion 129 and secure the vascular access device 200 in the holding cavity 110. Once rotated, the open portion on the second part 126 functions as an access point allowing tubing 220 to exit the side of the holding cavity. Once rotated to that that the open potions are no longer aligned, the security sticker 169 is secured to span the first part 125 and second part 126, like shown in FIG. 5*b*.

The security sticker 169 could be formed from a permanent adhesive or other security label such that removal of the label would permanently damage or destroy the security sticker 169. Also, attempts to rotate the first part 125 relative to the second part 126 to gain alignments of the full open portion 129 to access the vascular access device 200 would destroy or tear the sticker 169. Either way, tampering would be apparent.

Figure 6:
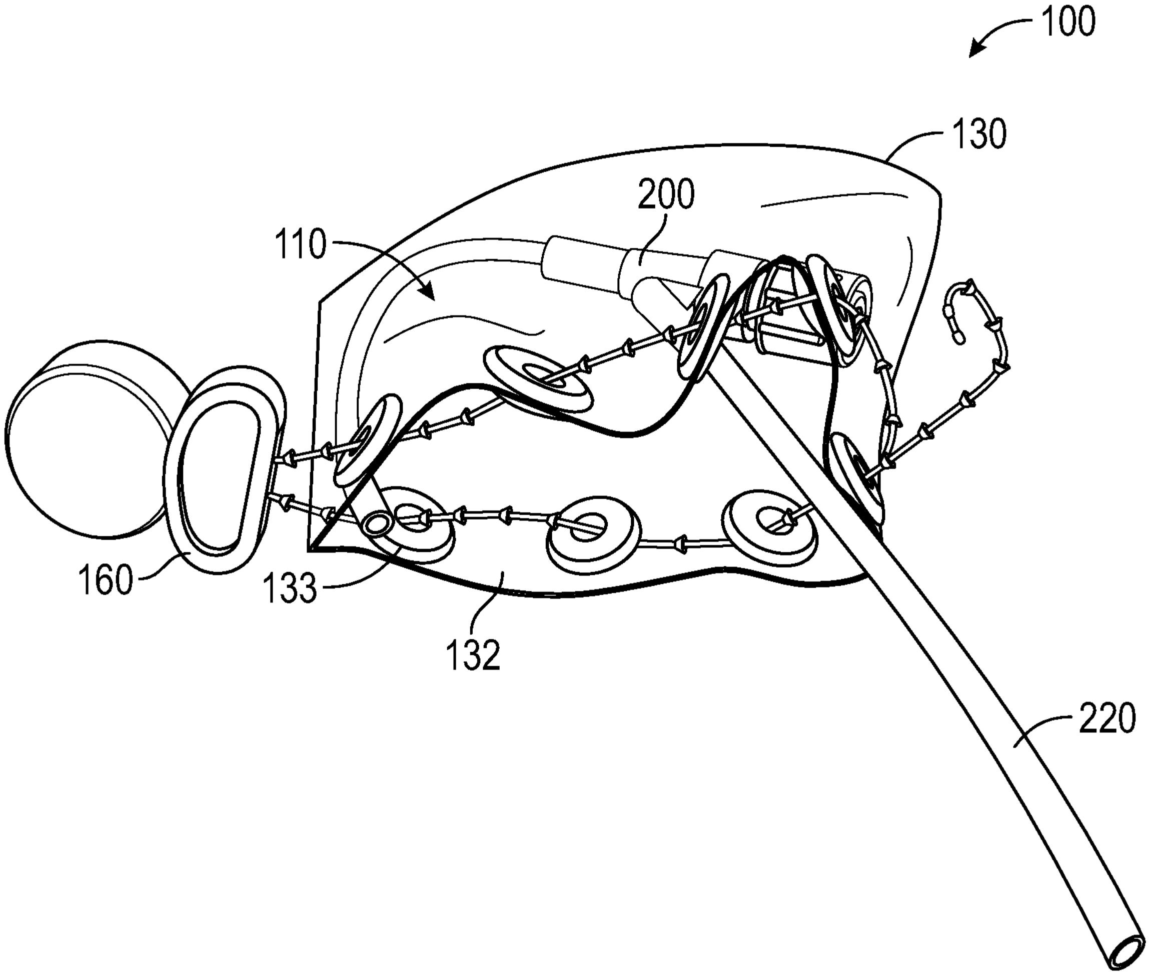
FIG. 6 is a perspective view of another embodiment of a tamper-evident closure comprising a bag with a securing mechanism cinched to irreversibly close the opening of the bag.

FIG. 6 is a perspective view of another embodiment of a tamper-evident closure 100 where the holding cavity 110 comprises a bag 130 with an opening 132 and a securing mechanism 160 cinched to irrevocably close the holding cavity 110.

In this embodiment, the holding cavity 110 is formed from a bag 130 with an opening 132. When open, the vascular access device 200 is inserted into holding cavity 110 of the bag 130. A bag 130 can advantageously accommodate a wide range of sizes and shapes of vascular access devices 200 and easily allow tubing 220 to exit through the opening 132. The securing mechanism 160 cinches at the opening 132 of the bag 130 to close the opening 132. At the opening 132 is a series of rivets 133 and the securing mechanism 160 is threaded through the rivets 133. Alternatively, slits or cuts in the bag or a channel of folded material of the bag could also hold the securing mechanism. The securing mechanism 160 allows for one-way tightening of the opening, such as a zip-tie with locking receiver as shown. In this embodiment, the cinching mechanism has two strips passing through the one-way locking unit. Further, one end of the securing mechanism 160 could include a breaking device, cutting ends, or tool for aiding in breaking the securing mechanism 160. The holding cavity 110 will become exposed when either the bag 130 is broken open or when the securing mechanism 160 is broken. Either way, tampering would be apparent.

When the holding cavity can be formed from a film, such as shown in FIG. 6, the bag could be constructed from a puncture resistant material such as Kevlar™ film. Then if a locking securement mechanism, such as a wire with a lock, is used, the tamper-evident closure, could be tamper-resistant or tamper-proof.

Figure 7A:
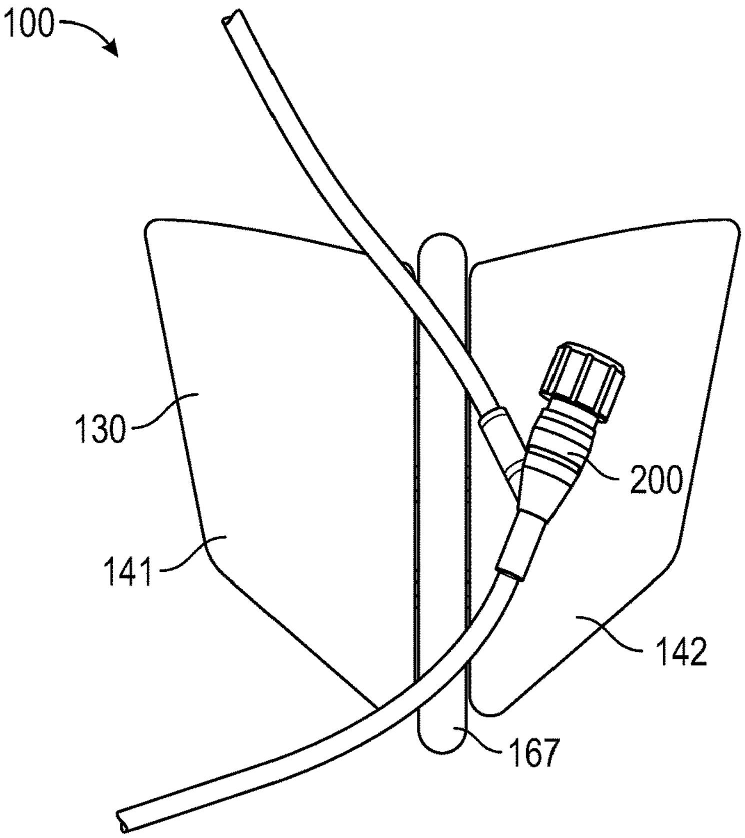
FIG. 7*a* is a perspective view of another embodiment of a tamper-evident closure comprising a conformable adhesive film with a set of perforations.
Figure 7B:
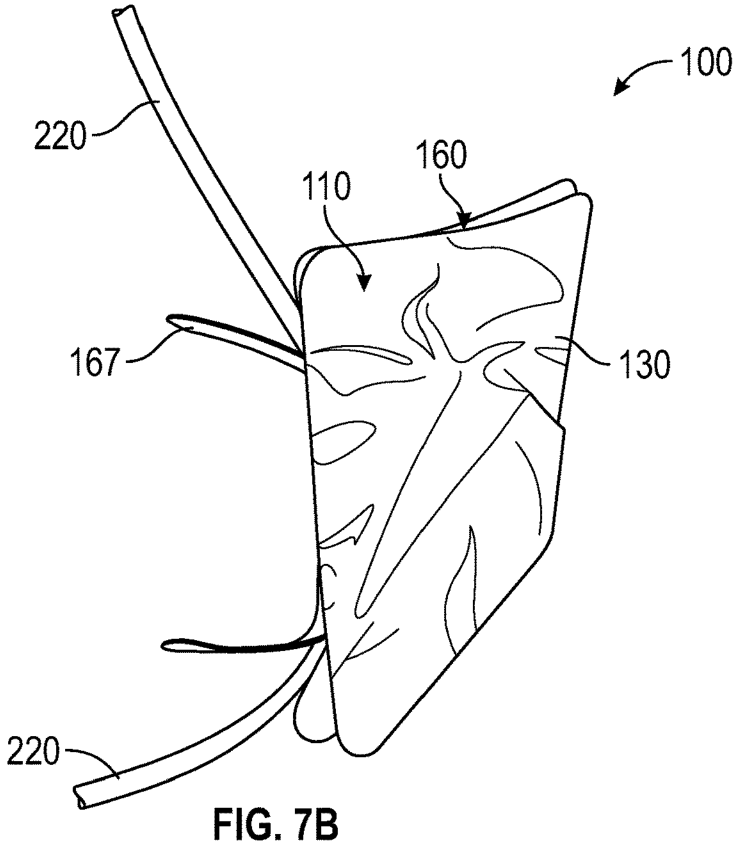
FIG. 7*b* is a perspective view of the tamper-evident closure of FIG. 8*a* with a vascular access device within the folded film to irreversibly contain the vascular access devices.

FIG. **7*a* is a perspective view of another embodiment of a tamper-evident closure 100 comprising a conformable adhesive film that when formed around the access device 220 creates a bag 130. FIG. 7*b* is a perspective view of the tamper-evident closure 100 of FIG. 7*a* with the conformable adhesive film folded to irreversibly contain the vascular access device 200**.

In this embodiment, the holding cavity 110 is formed from the film of the bag 130 with an first adhesive surface 141 folding to a second adhesive surface 142. As shown in FIG. **7*a*, the vascular access device 200 is applied on the bag 130, and then folded around the vascular access device 200 to create the holding cavity 110 in the bag 130 surrounding the vascular access device 200. The securing mechanism 160 is opposing first surface 141 and second surface 142 adhesively secured together that will seal the bag 130 around the vascular access device 200, such as shown in FIG. 7*b***.

The adhesive should be a permanent adhesive, so that the opposing adhesive faces cannot be opened. In some embodiments, the permanent adhesive is a contact adhesive. Prior to use, the adhesive surface could be covered and protected with a removable release liner. The holding cavity 110 will become exposed when the bag 130 is broken open. In some instances, a release material can be used so that the two adhesive surface will adhere, but following separation, one of the adhesives preferentially attract to the other adhesive surface leaving no adhesive on the release containing surface. In this case, the two surfaces cannot secured together.

Figure 8B:
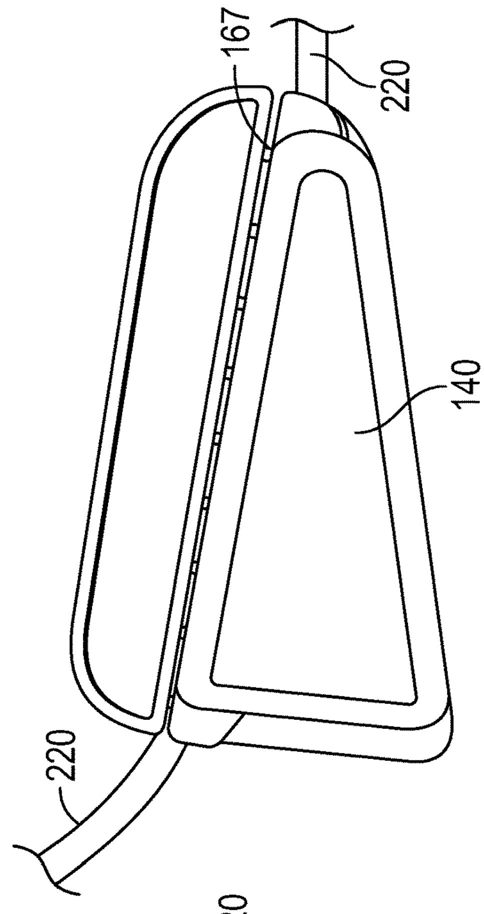
FIG. 8*b* is a perspective view of the tamper-evident closure of FIG. 8*a* closed and containing the vascular access device.
Figure 8A:
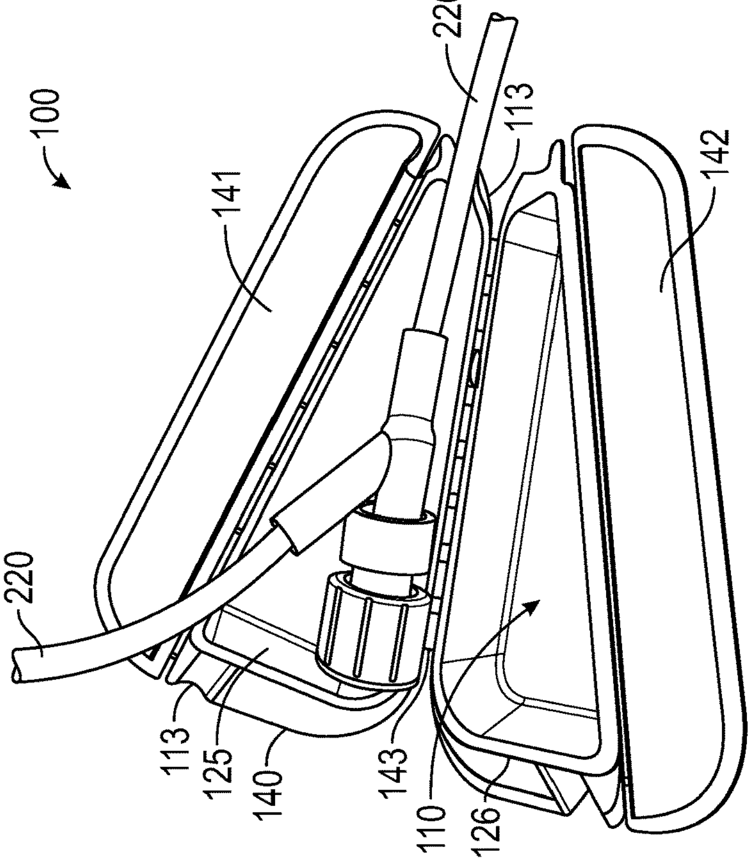
FIG. 8*a* is a perspective view of another embodiment of a tamper-evident closure comprising an envelope opened to receive a vascular access device.

In some embodiments, such as shown in FIG. 8B, a tear strip 167 is included. In this embodiment, the tear strip 167 is in the center of the bag 130, which allows the film to be easily applied around the vascular access device 200 without having to seal all edges. Also, the tear strip 167 makes for easy opening of the formed bag 130 to remove the vascular access device 130. When desiring to open the bag 130, the tear strip 167 is removed from the bag 130 to expose the vascular access device 200. Then, the bag 130 cannot be reclosed.

The adhesive should be a permanent adhesive, so that the opposing surfaces cannot be separated. In some embodiments, the permanent adhesive is a contact adhesive, which is an adhesive that strongly adheres to itself but typically does not adhere to other substrates. A contact adhesive works well so that the exposed adhesive does not stick to the vascular access device and does not transfer adhesive to the surface of the vascular access device making that device sticky and dirty. Also, medical providers often wear gloves, and a contact adhesive, will not strongly adhere to the worker's gloves will strongly adhere to another surface containing contact adhesive. An example of a suitable film with a contact adhesive is 3M™ SCOTCH™ Flex & Seal Shipping Roll, available from 3M Company. Prior to use, the adhesive surface could be covered and protected with a removable release liner.

FIG. **8*a* is a perspective view of another embodiment of a tamper-evident closure 100 comprising a holding cavity 110 that is an envelope 140. FIG. 8*b* is a perspective view of the tamper-evident closure 100 of 8*a* closed and containing the vascular access device 200**.

These constructions described as an envelope are structurally similar to the bag constructions, but as shown in the images these envelop constructions are slightly more rigid, with more structural integrity as compared to thin-film bag constructions. A structurally rigid tamper-evident closure could be formed from a plastic in a molding, printing, or thermoforming process. A more structurally rigid tamper-evident closure has more form for receiving the access device into the correct position withing the holding cavity and can easily close. Any of these envelope constructions could instead be formed form films.

The envelope 140 includes a first part 125 and second part 126 connected along a fold line 143. As shown, access points 113 can be molded into the tamper-evident closure 110, in one or both of the first or second parts 125, 126 to more easily accommodate the exiting tubing 220. On the first part 125 is a first adhesive surface 141 and on the second part 126 is a second adhesive surface 142. The access device 200 is inserted into the holding cavity 110, and the first part 125 is hinged toward the second part 126. The first adhesive surface 141 contacts the second adhesive surface, as shown in FIG. **8*b* to close the tamper evident closure 100. When desiring to open the envelope 140, the sealed adhesive surfaces 141, 142 are removed from the envelope 140 at a tear strip 167 located between the holding cavity 110 and the sealed adhesive surfaces 141, 142**. Then, the envelope cannot be reclosed, and tampering would be apparent.

Figure 9:
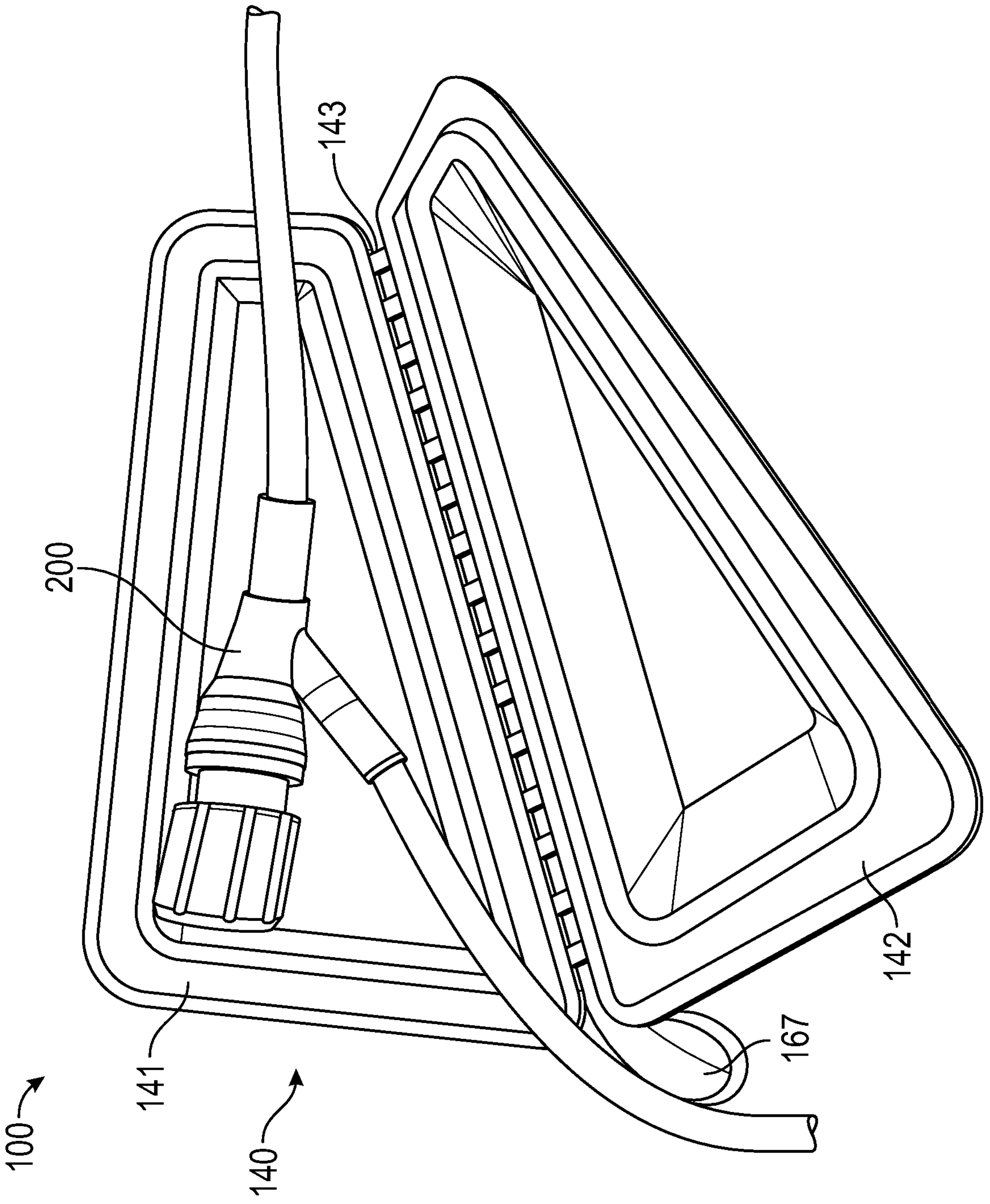
FIG. 9 is a perspective view of another embodiment of a tamper-evident closure comprising an envelope opened to receive a vascular access device.

FIG. 9 is a perspective view of another embodiment of a tamper-evident closure 100 comprising an envelope 130 open to receive a vascular access device 200. This embodiment is substantially similar to the embodiment shown in FIGS. **8*a-b*. However, in this embodiment, fold line 142 between the first part 125 and second part 126 is the tear strip 167. After the vascular-access device 200 is inserted, then the tamper-evident closure 100 is hinged closed so the adhesive surfaces 141, 142 contact one another to seal the tamper-evident closure 100. When desiring to open the envelope 140, the tear strip 167 is removed, disconnecting the first part 125 from the second part 126 to expose the vascular access device 200. Then, the envelope 140** cannot be reclosed.

Figure 10:
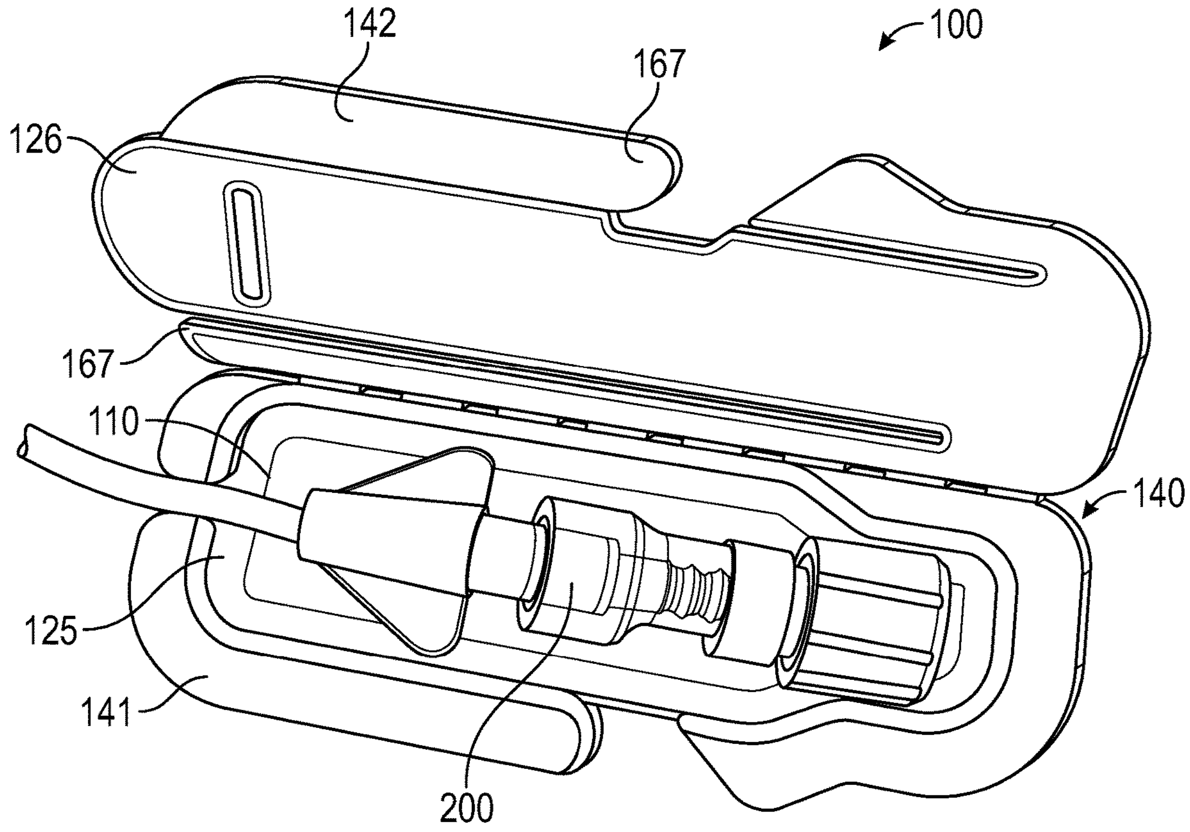
FIG. 10 is a perspective view of another embodiment of a tamper-evident closure comprising an envelope open to receive a vascular access device.

FIG. 10 is a perspective view of another embodiment of a tamper-evident closure 100 comprising a holding cavity 110 in the form of an envelope 140. This embodiment is similar to the embodiment described in FIGS. 8*a*, 8*b*, and FIG. 9 because the tamper-evident closure 100 is formed from a structurally rigid material forming an envelope 140 for receiving the vascular access device 200. In this embodiment, the tamper-evident closure 100 has a first part 125 with a first adhesive surface 141 and a second part 126 with a second surface 142. The second part 126 hinges over the first part 125 to close the holding cavity 110 such that the first surface 141 and second surface 142 adhesively seal together. A tear strip 167 is adjacent to the holding cavity 110 such that when desiring to open the envelope 140, the tear strips 167 are removed to expose the vascular access device 200. Then, the envelope 140 cannot be reclosed.

Figure 11:
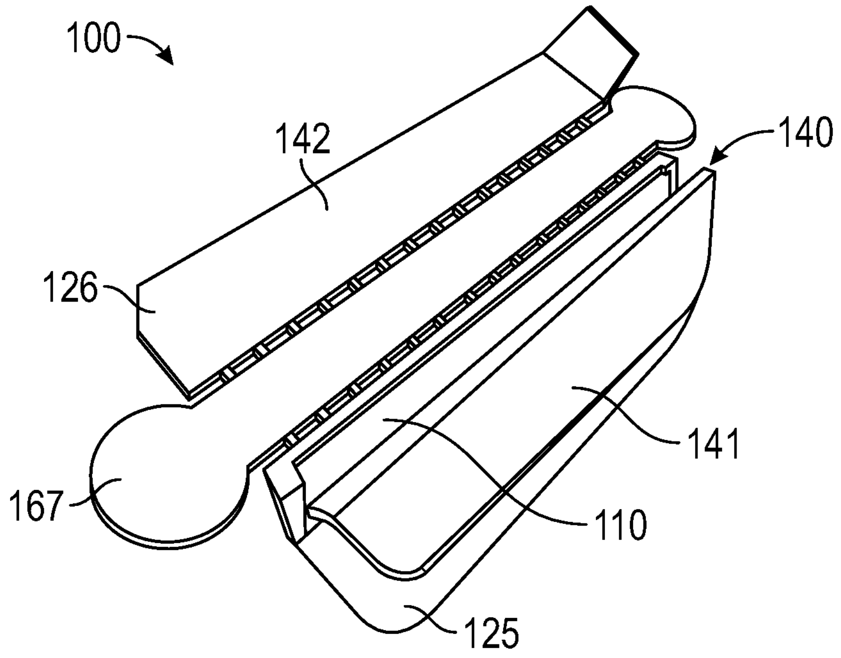
FIG. 11 is a perspective view of another embodiment of a tamper-evident closure comprising an envelope open to receive a vascular access device.

FIG. 11 is a perspective view of another embodiment of a tamper-evident closure 100 comprising a holding cavity 110 that is in the form of an envelope. This embodiment is similar to the embodiment described in FIGS. 8*a*, 8*b*, 9, and 10 because the tamper-evident closure 100 is formed from a structurally rigid material forming an envelope 140 for receiving a vascular access device. The tamper-evident closure 100 is pinched to open the holding cavity 110. The holding cavity 110 has a first part 125 with a first surface 14 land a second part 126 with a second surface 142 that are hingedly connected and when in contact with one another are adhesively secured to close and seal the holding cavity 110 after the vascular-access device is inserted. In this embodiment, the tear strip 167 overlaps the first part 125, so that when desiring to open the envelope, the tear strip can be removed to expose the vascular access device. Then, the envelope 140 cannot be reclosed.

Figure 12A:
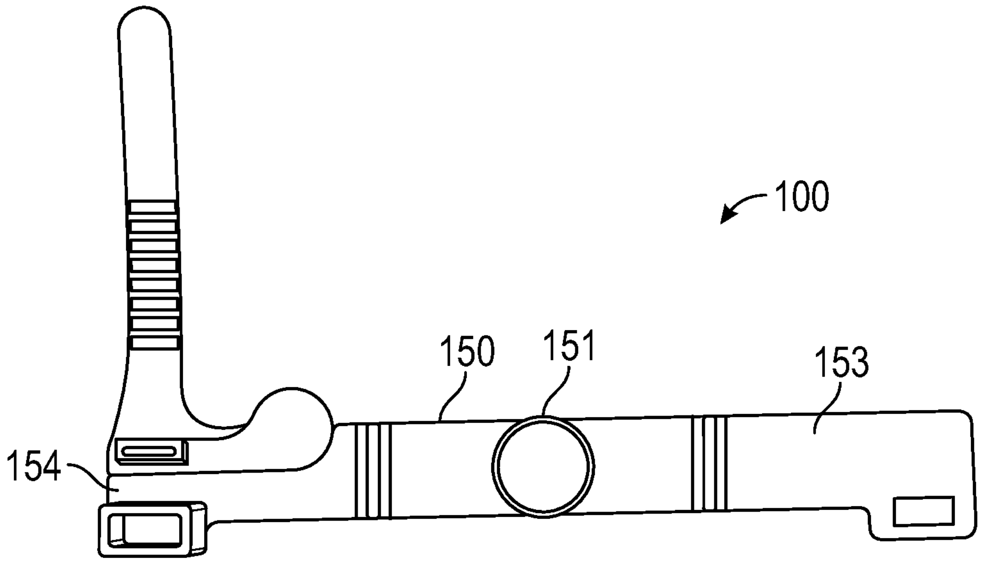
FIG. 12*a* is a perspective view of another embodiment of a tamper-evident closure comprising a base and straps.
Figure 12B:
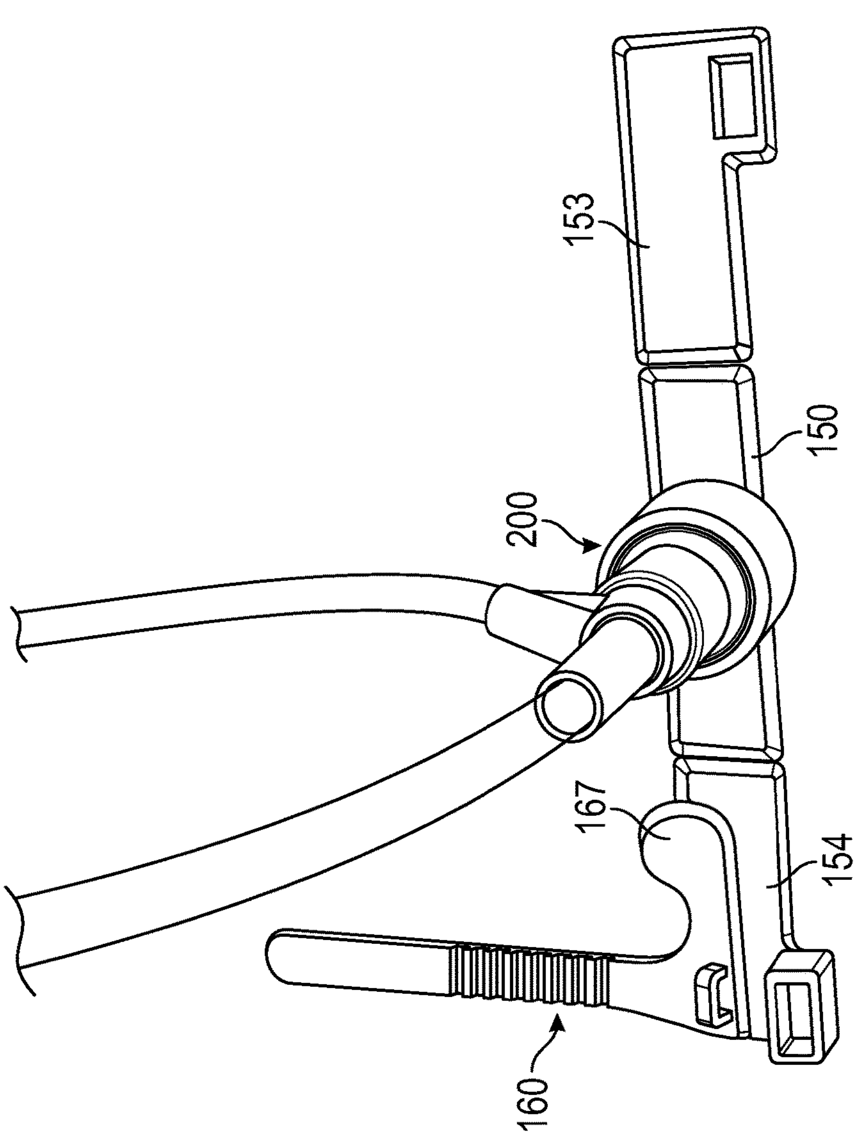
FIG. 12*b* is a perspective view of the tamper-evident closure of FIG. 12*a* with a vascular access device connected with the base of the tamper-evident closure.
Figure 12C:
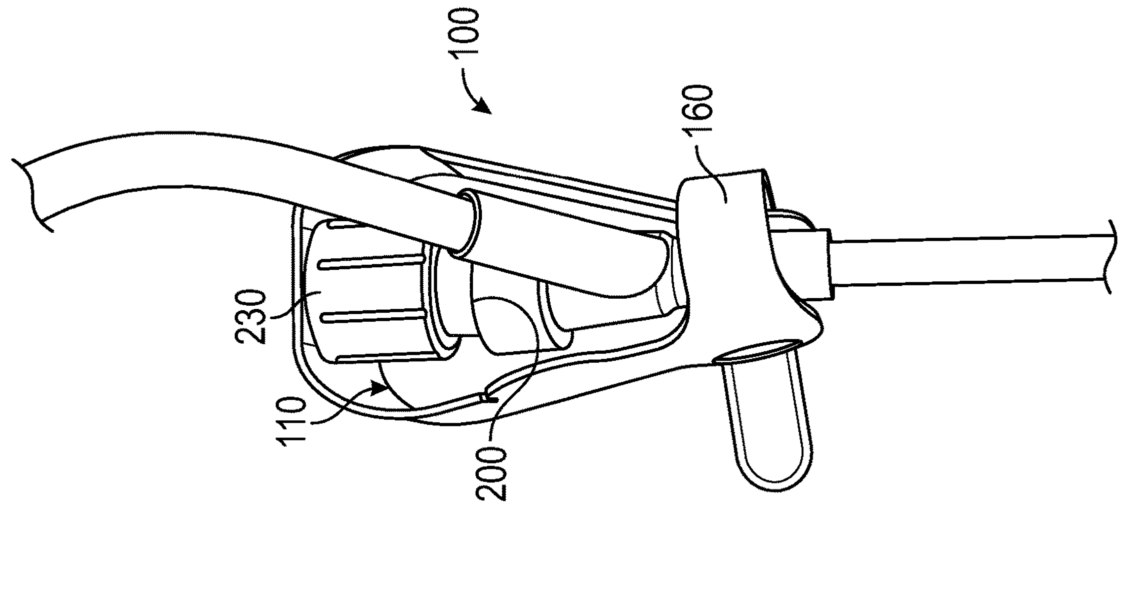
FIG. 12*c* is a perspective view of the tamper-evident closure of FIG. 12*b* with the straps forming the securing mechanism cinched to irreversibly contain the vascular access device.

FIG. 12*a* is a perspective view of another embodiment of a tamper-evident closure 100 where the holding cavity 110 comprises a base 150 and extending from the base 150 is a first strap 153 and a second strap 154. FIG. 12*b* is a perspective view of the tamper-evident closure 100 of FIG. 12*a* with a vascular access device 200 connected with the base 150 of the tamper-evident closure 200. FIG. 12*c* is a perspective view of the tamper-evident closure 100 of FIG. 12*b* with the straps 153, 154 secured together with securing mechanism 160 to form the holding cavity 110.

In this embodiment, the holding cavity 110 has a base 150 and opposing first and second straps 153, 154, where the vascular access device 200 is position adjacent to the base 150 and the opposing straps 153, 154. A holding cavity 110 such as showing in FIG. 12*c* is well suited to engage with a cap 230 covering a needleless connector on a vascular access device 200. In this embodiment, the base 150 includes protruding portion 151 that integrally engages into the cap 230, and in particular into a recessed portion of the cap 230. The securing mechanism 160 is an ratcheting mechanism that engages with matching opening the first and second straps 153, 154, as best shown in FIG. 12*c*. When the securing mechanism 160 is engaged, the first and second straps 153, 154 tightly fit around the access device 200. The first and second straps 153, 154 are long enough such where the securing mechanism 160 is tightened, the straps 153, 154 are adjacent to outwardly extending portions of the access device 200. Therefore, the tamper-evident closure 100 cannot pulled down to disengage from connection with the cap 230. When the base 150 is engaged and the first and second straps 153, 154 are closed, the vascular access device 200 is inaccessible unless the securing mechanism 160 is irreversibly broken. To aid in helping to intentionally break the strap, tear strips 167 can be included on one or both straps. Pulling on the tear strip 167 breaks the strap so it can be disconnected without the use of a tool.

Figure 13:
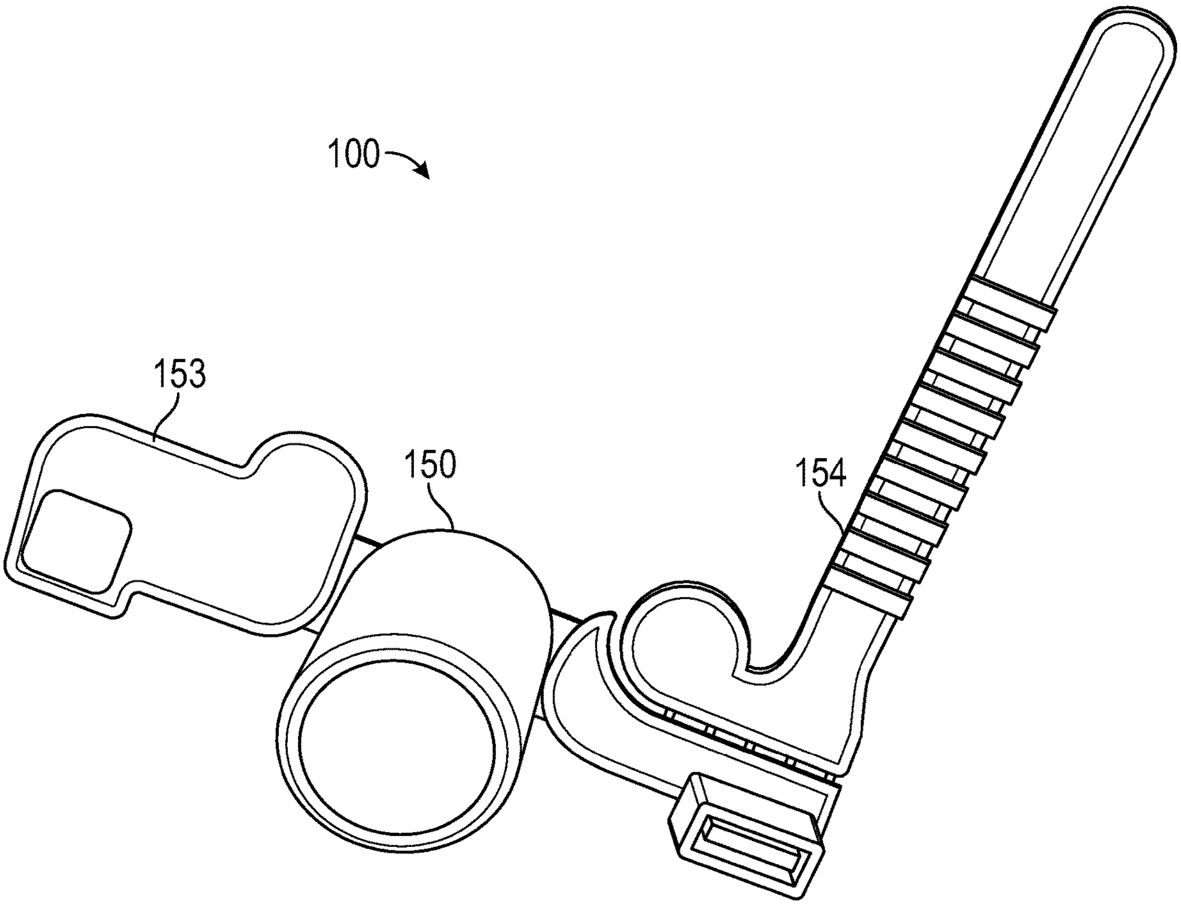
FIG. 13 is a perspective view of another embodiment of a tamper-evident closure comprising a base and straps.

FIG. 13 is a bottom perspective view of another embodiment of a tamper-evident closure 100 comprising a base 150 and opposing first and second straps 153, 154, similar to the embodiment in FIGS. 12*a*-12*c*. In this embodiment, the base 150 encloses around a disinfecting cap with the straps 153, 154 securing to the top part of the base 150. Therefore, there is more vertical tolerance for movement before the base 150 might entirely dislodge from covering the cap. In this embodiment, the base 150 could be the cap to engage with the needleless connector on the vascular access device. The cap may include an internal securing mechanism for engaging with the needleless connector. The cap may include an antiseptic for keeping the needleless connector clean and ready for use when the cap is removed. This would allow the integration of the disinfecting process and tamper securing process to be integrated into a single step.

Figure 14:
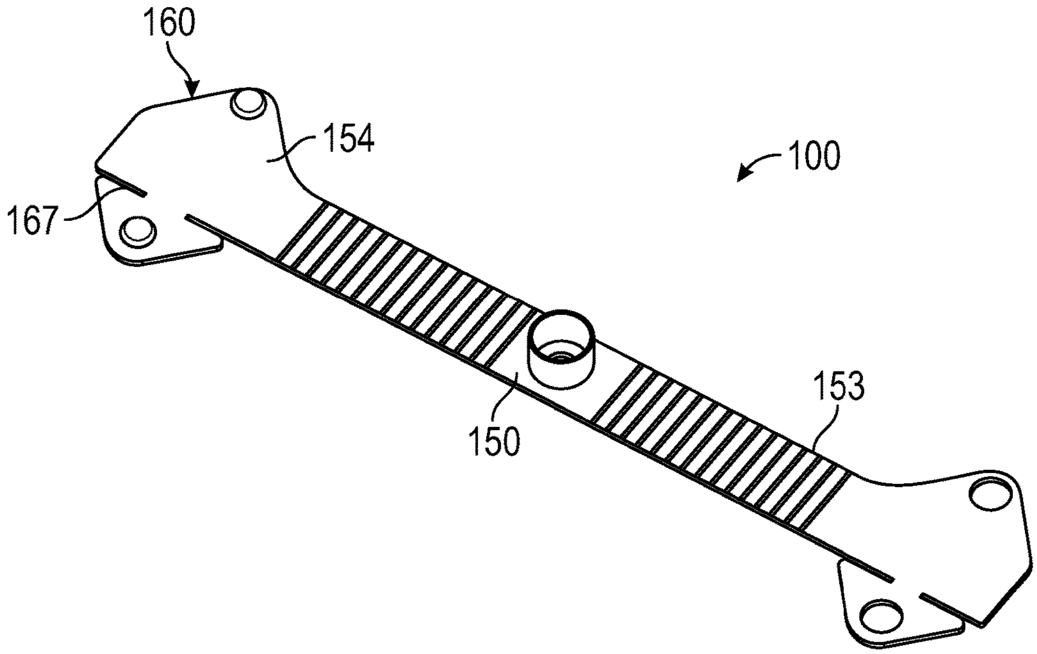
FIG. 14 is a perspective view of another embodiment of a tamper-evident closure comprising a base and straps.

FIG. 14 is a perspective view of another embodiment of a tamper-evident closure comprising a base 150 and straps 153, 154. This embodiment is substantially similar to the embodiment in FIGS. 12*a*-12*c*. This embodiment is similar to the embodiment described in FIG. 9*a*-9*c*. However, in this embodiment, the securing mechanism 160 is at the first strap 153 a set of recesses that interlock with protrusions at the second strap 154. To aid in helping to intentionally break the secured together straps 153, 154, perforation lines 167 can be included on one or both straps 153, 154. In this embodiment, cut lines at one of the protrusion/recess can be twisted from the tamper-evident closure 100 to irreversibly open the holding cavity.

Figure 15:
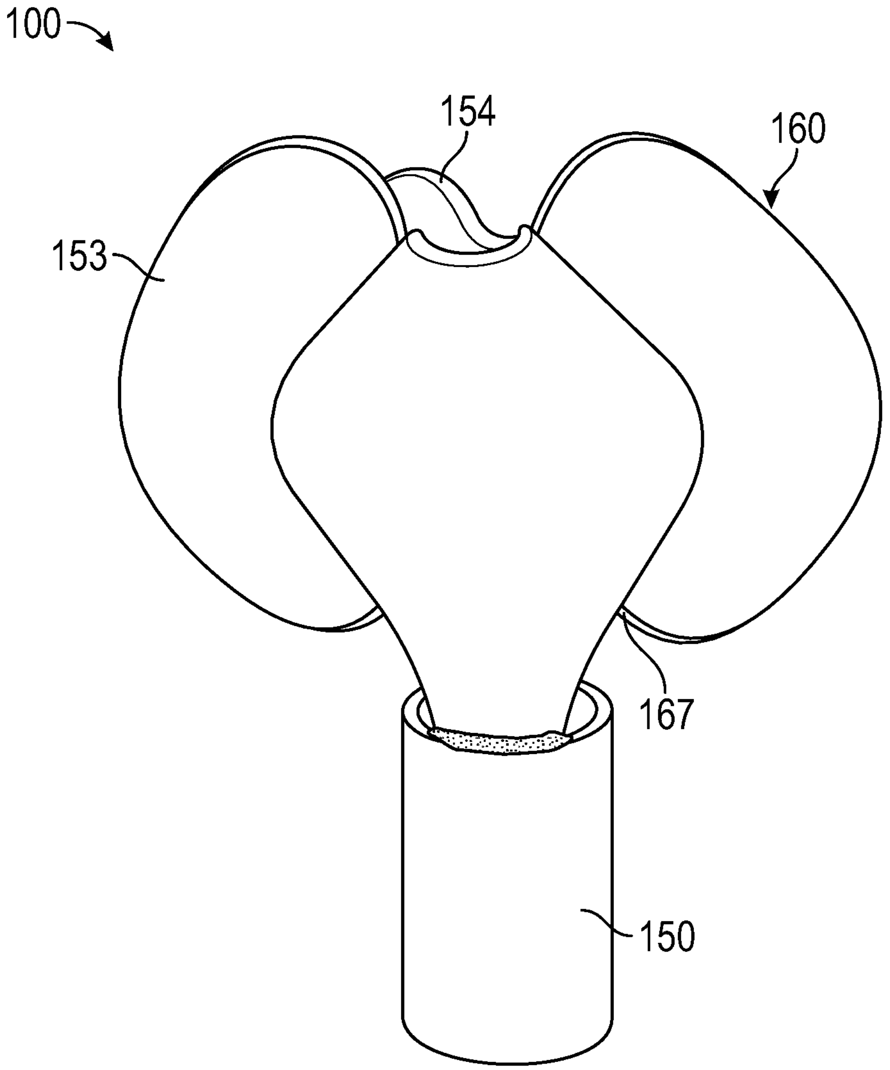
FIG. 15 is a perspective view of another embodiment of a tamper-evident closure comprising a base and straps.

FIG. 15 is a perspective view of another embodiment of a tamper-evident closure 100 comprising a base 150 and straps 153, 154 substantially similar to the embodiment shown in FIGS. 12*a*, 12*b*, 12*c*, 13, and 13, however with the straps 153, 154 adhesively connected. The securing mechanism 160 are opposing adhesive faces on the straps 153, 154 that will seal together. Since there are many different manufacturers of connectors, this allows for a flexible securing system to compensate for mechanical variability. The adhesive should be a permanent adhesive, so that the opposing adhesive faces cannot be opened. In some embodiments, the permanent adhesive is a contact adhesive. Prior to use, the adhesive surface could be covered and protected with a removable release liner. To aid in helping to intentionally break the strap, perforation lines 167 can be included on one or both straps.

Tamper-evident closures, such as those disclosed in this application, are designed to be removed without the need for additional removal tools. For example, perforation lines, breakable securement straps, twistable or tearable structures or film can be used so that when a health care provider intentionally wants to access the vascular access device, it is easy to remove the tamper-evident closure. Also, it is desirable that when the tamper-evident closure is intentionally removed that the holding cavity opens cleanly with few separating parts. For example, in the embodiments described in FIGS. 12*a*-15, the base can be twisted to remove from the straps for a clean separation.

In embodiments where a film could be used for creating all or a part of the tamper-evident closure, an attempt at tampering could be made to tear, rip, pull open the film itself, or peel apart the two film surfaces that have joined or closed together. It may be desirable to include a film that has properties that will show tampering. For example, the film could have preferential tearing in one or more directions. Areas of weakness, manufacturing orientation of the film, embossing, are all ways that a film could have preferential tearing. In such an instance, as tampering is attempted, then a clean tear in the film in a direction will be made showing apparent tampering.

In another embodiment, where the film that has properties that will show tampering, the film could have a physical change upon stress, stretching, or pulling. For example, a film may be transparent or semi-transparent and upon stretch in any direction the film can transition to opaque. This will visually show that the film has been tampered or attempted at tampering.

As described, and would be apparent to one of skill, rigid structures, locking securement mechanisms. For example, the health care provider would have access to the lock to release the securing mechanism.

Although specific embodiments have been shown and described herein, it is understood that these embodiments are merely illustrative of the many possible specific arrangements that can be devised in application of the principles of the invention. Numerous and varied other arrangements can be devised in accordance with these principles by those of skill in the art without departing from the spirit and scope of the invention. The scope of the present invention should not be limited to the structures described in this application, but only by the structures described by the language of the claims and the equivalents of those structures.

What is claimed is:

1. A tamper-evident closure, comprising:

a first part and a second part that co-operatively form a holding cavity;

a protruding channel extending along a portion of the first part;

a receiving channel defined in a portion of the second part, wherein the protruding channel is configured to align and engage with the receiving channel; and a tear strip connected between one of (i) the protruding channel and the first part or (ii) the receiving channel and the second part, wherein the tear strip is configured to disconnect from the one of the first part or the second part, wherein the tamper-evident closure defines an access point and at least a portion of a medical access device is extendable through the access point into the holding cavity, and wherein the tear strip comprises a channel locking fit that includes a plurality of teeth, and wherein the second part defines a plurality of cavities sized to receive the plurality of teeth.

2. The tamper-evident closure of claim 1, where the tear strip is between the protruding channel and the first part, and wherein removal of the tear strip is configured to:

disconnect the tear strip from the first part; and disengage the protruding channel from the receiving channel.

3. The tamper-evident closure of claim 1, wherein the first part is pivotally, slidably, or rotatably connected with the second part.

4. The tamper-evident closure of claim 1, further comprising a tab connected with the tear strip, wherein actuation of the tab is configured to disengage the tear strip from the first part or the second part.

5. The tamper-evident closure of claim 1, further comprising front tabs extending on each side of the access point.

6. The tamper-evident closure, of claim 1, wherein the access point is a first access point and wherein the tamper-evident closure further defines a second access point that is not longitudinally aligned with the first access point.

7. The tamper-evident closure of claim 6, further comprising a door configured to cover the second access point.

8. The tamper-evident closure of claim 7, wherein the door is slidably connected to the second part to cover or expose the second access point.

9. The tamper-evident closure of claim 1, wherein the medical access device comprises a fluid delivery tube, and wherein the fluid delivery tube is configured to pass through the access point.

10. The tamper-evident closure of claim 1, wherein the plurality of teeth is receivable in the plurality of cavities to define a zig-zag line along a portion of the tamper-evident closure.

11. A method, comprising;

inserting, into the tamper-evident closure of claim 1, the medical access device; and engaging the protruding channel of the first part with the receiving channel of the second part.

12. A tamper-evident closure, comprising:

a first part and a second part rotatably coupled on a first side of the tamper-evident closure, wherein the first part and the second part co-operatively define a holding cavity and an access point through the first part and the second part into the holding cavity, and wherein at least a portion of a medical access device is extendable through the access point and into the holding cavity;

a protrusion extending along a portion of the first part on a second side of the tamper-evident closure;

a receiving channel defined along a portion of the second part on the second side, wherein the protrusion is receivable within the receiving channel;

a tear strip connected between (i) the protrusion and the first part or (ii) the receiving channel and the second part, wherein the tear strip is disconnectable from the first part or the second part, and wherein the tear strip comprises a channel locking fit that includes a plurality of teeth, and wherein the second part defines a plurality of cavities sized to receive the plurality of teeth.

13. The tamper-evident closure of claim 12, wherein the first part is rotatable relative to the second part between an open position and a closed position, wherein the protrusion is received in the receiving channel to maintain the first part in the closed position, and wherein the tear strip is decouplable from the first part or the second part to allow the first part to transition to the open position.

14. The tamper-evident closure, of claim 12, wherein the access point is a first access point and the tamper-evident closure further defines a second access point that is longitudinally mis-aligned with the first access point.

15. The tamper-evident closure of claim 14, further comprising a door configured to cover the second access point.

16. The tamper-evident closure of claim 15, wherein the door is slidably connected to the second part to cover or expose the second access point.

17. The tamper-evident closure of claim 12, further comprising a front tab extending on each side of the access point.

18. The tamper-evident closure of claim 12, wherein the plurality of teeth is receivable in the plurality of cavities to define a zig-zag line along a portion of the tamper-evident closure.

* * * * *